United States Patent [19]
Gentelia et al.

[11] Patent Number: 5,135,506
[45] Date of Patent: Aug. 4, 1992

[54] CANNULA HOLDING DEVICE

[75] Inventors: John Gentelia, Madison; James C. Calenzo, Sr.; Frank Williams, both of Utica, all of N.Y.

[73] Assignee: Conmed Corporation, Utica, N.Y.

[21] Appl. No.: 712,738

[22] Filed: Jun. 10, 1991

[51] Int. Cl.$^5$ ............................................. A61M 25/02
[52] U.S. Cl. .......................... 604/180; 128/DIG. 26
[58] Field of Search .......................... 604/180, 179; 128/DIG. 26

[56] References Cited

U.S. PATENT DOCUMENTS

| | | | |
|---|---|---|---|
| 4,324,237 | 4/1982 | Buttaravoli | 604/180 |
| 4,490,141 | 12/1984 | Lacko et al. | 604/180 |
| 4,534,762 | 8/1985 | Heyer | 604/180 |

Primary Examiner—John D. Yasko
Attorney, Agent, or Firm—Larson & Taylor

[57] ABSTRACT

A cannula holder is provided to maintain a cannula in a fixed position on body tissue while also allowing the cannula to be reoriented with respect to an incision. The cannula holder comprises a pad having a large surface area with integral finger shaped projections extending from the pad. The fingers form a V shaped projection from the pad. There are concave regions formed on the outer circumference of the pad adjacent to the fingers for allowing the fingers to bend around the outer surface of a cannula. A means for securing the cannula holder to a patient's skin is provided by an adhesive layer that is attached to the pad. This adhesive layer is also on the fingers so that the fingers may be adhesively attached to the cannula. A removable paper layer is provided to cover the adhesive layer to prevent the adhesive layer from drying or accidently securing to objects.

11 Claims, 1 Drawing Sheet

CANNULA HOLDING DEVICE

FIELD OF THE INVENTION

This invention relates generally to a cannula holding device and more specifically, to a specifically shaped adhesive pad for maintaining a cannula in operative position with respect to body tissue through which the cannula extends by securing the cannula to the patient's skin.

BACKGROUND OF THE INVENTION

In performing laproscopic surgery, an incision is made in a patient by a trocar to admit a cannula which serves as a conduit for the introduction of selected surgical instruments into a body cavity. During the surgical procedure, several cannulas may be directed into a patient at spaced locations to facilitate simultaneous use of a number of instruments. The body cavity in which the operation is performed is filled with a gas to expand the surrounding tissue to create a suitably sized operating space.

In the operating procedure, there are several major concerns. First, it is important to confine the gas used to expand the cavity in which the operation is to be performed. Deflation of the body cavity could result in interruption of a surgical procedure and/or injury to the patient.

It is important to maintain the cannula to be positively positioned on the body tissue through which it passes.

It is also important that the cannula be permitted to be reoriented with respect to the body cavity to maximize the working range for each instrument.

It is desirable to avoid traumatizing the skin surrounding the cannula so that recovery from the surgery is expedited.

Unfortunately, the above objectives are in conflict. In laproscopic surgery, the laparoscope is constantly moved, in and out, and side to side, to follow the procedure. During movements of the laparoscope, exudate accumulates in the cannula causing more drag and thus increasing the potential of pulling the cannula out of the patient. If the cannula is pulled out of the patient, the abdominal cavity will deflate and cause a delay while the insufflation pressure is reestablished. The trocar has to be reinserted, to reposition the cannula, causing additional trauma to the placement site.

By securing the cannula to the patient the risk of accidentally removing the cannula is reduced. However, there is additional trauma associated with prior art devices that have been used to secure the cannula. There is also a greatly reduced ability to reorient the cannula within the incision with such prior art devices.

There are a number of prior art patents disclosing devices utilized to solve the above noted problems. U.S. Pat. No. 5,002,557 (Hasson) discloses the use of a balloon or membrane that is attached to the base of a cannula. When the cannula is inserted into a patient, the membrane or balloon is inflated so as to increase the surface area of the base beyond that of the original insertion. This device adds additional complexity to a cannula that is discarded after each operation and thus increases the cost of the operation.

U.S Pat. No. 4,593,681 (Soni) discloses the use of a stabilizing plastic sheath that has a hole therein to accept an endoscope. This sheath has a locking mechanism to hold the endoscope in place. This device significantly reduces the ability of a surgeon to reorient an endoscope within an incision.

In a similar fashion, U.S. Pat. No. 2,350,775 discloses a cannula holder that positively locks a cannula in a particular position by a frame that is attached to the cannula.

U.S. Pat. No. 3,817,251 (Hasson) discloses an adjustable cone shaped sleeve for blocking the incision gap. The cannula is held in place by a pair of hooks that receive sutures attached to the patient. The use of sutures does aid in the positioning of the cannula but adds to the traumatizing of the surrounding tissue.

U.S. Pat. No. 3,253,594 (Matthews) discloses the use of an inflatable balloon in combination with a disk for holding a cannula in place. The balloon is inserted into the patient through an incision and then inflated to come into contact with the inside surface of the body cavity. The disk is attached to the balloon on the exterior of the patient's body. The disk has threads which engage a cap that is used for tightening the disk down upon the body. Thus, the balloon and disk combination are designed to create a frictional grip on the skin of the patient adjacent to the incision. This gripping tends to cause traumatizing to the skin.

Several patents disclose various ways to secure catheters to a patient. These patents include 4,324,236 (Gordon et al.); 4,985,018 (Smith); 4,737,143 (Russell); 4,669,458 (Abraham et al) and 3,670,727 (Reiterman). Theses devices would not function properly for holding a cannula since a cannula must have the ability to be reoriented in or out and side to side of the incision. The above devices are designed to secure a catheter to a patient so as to prevent the catheter from moving.

SUMMARY OF THE INVENTION

According to the invention, a cannula holder is provided which has a number of advantages including not traumatizing the patient, maintaining the cannula in a fixed position while also allowing the cannula to be reoriented with respect to an incision. The cannula holder according to the present invention comprises a pad having a large surface area and having first and second finger shaped projections extending from the pad. The finger shape projections are integral elements of the pad and form a roughly V shaped configuration. There are concave cut-out portions formed on the outer circumference of the pad adjacent to the outer edges of the fingers for allowing the fingers to bend around an outer surface of a cannula disposed at a right angle with respect to the surface of the pad. A means for securing the cannula holder to a patient's skin is provided by an adhesive layer that is attached to the pad. This adhesive layer continues along the fingers so that the fingers may be adhesively attached to the cannula. A removable paper layer is provided to cover the adhesive layer to prevent the adhesive layer from drying or accidently securing to objects.

This device is a significant improvement over the prior art in that it allows a surgeon to quickly secure a cannula to the skin of a patient adjacent an incision and thus reduce the risk of accidentally pulling the cannula out of an incision. The device allows the surgeon to adjust the position of the cannula in the incision by allowing a limited degree of movement of the cannula in or out or side to side. The device aids in positively maintaining the cannula in the incision by sewing the cannula to the patient's skin. Another advantage to this device is that it is non-invasive and does not traumatize the skin around the incision, and thus decreases recovery time. This device is easy to apply and remove, and is less expensive that traditional cannula holders.

Other features and advantages of the invention will be set forth in, or apparent from, the following detailed description of the preferred embodiment of the invention.

DESCRIPTION OF THE PREFERRED EMBODIMENTS

Figure 1:
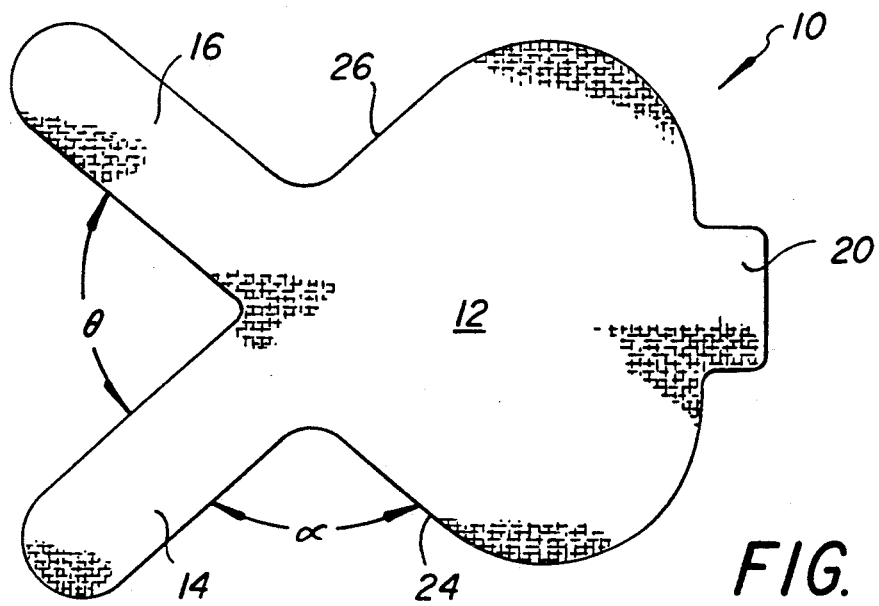
FIG. 1 is a top plan view of a cannula holding device constructed in accordance with a preferred embodiment of the invention.

Referring to FIG. 1, a cannula holder constructed in accordance with a preferred embodiment of the invention is generally denoted as element 10. The cannula holder 10, is composed of a body region 12 and two finger like extensions 14 and 16. Body 12 has a generally elliptical shaped central portion with an integral tab 20 disposed opposite the finger projections 14 and 16. The two finger extensions 14 and 16 which are integrally formed with the body 12 form a generally V shaped recess between the inner edges of the fingers 14 and 16. An angle $\Theta$ is formed between the inner edges of the two fingers 14 and 16. In a preferred embodiment, the angle $\Theta$ is in the range of 75°–85° and preferably is 80°. The outer edges 24 and 26 of base 12 taper to merge with the outer edges of fingers 14 and 16. An angle o is formed between the edges 24 and 26 and the outer edges of the fingers 14 and 16. In a preferred embodiment, the angle $\alpha$ is in the range of 80° to 95° and preferably is 90°. In the preferred embodiment, the body portion 12, tab 20 and fingers 14 and 16 of cannula holder 10 is a single integral piece. The shape of body 12 is designed to maximize the surface area that comes into contact with a patient's skin.

Figure 2:
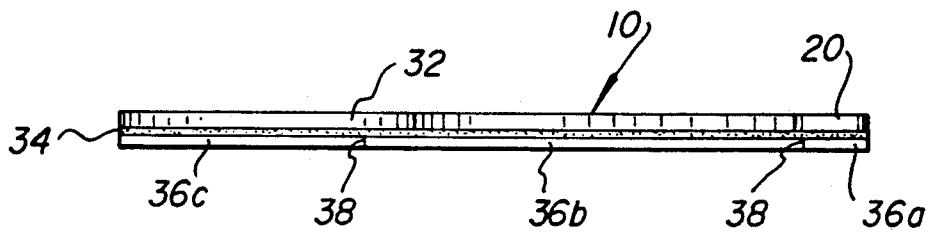
FIG. 2 is a side elevational view of the cannula holding device of FIG. 1.

The cannula holder 10 is constructed of several layers as may be seen in FIG. 2. The layer 32 is formed of a porous, hypoallergenic, material such as gauze or any other breathable sheet material known in the art. This layer has an approximate thickness of 0.015. An adhesive layer 34 is attached to layer 32. In a preferred embodiment, the adhesive layer is an integral part of the gauze layer 32. In an alternate embodiment, layers 32 and 34 are distinctly separate layers. Layer 36 is composed of a plurality of distinct parts. For the ease of illustration only three parts are shown and are labeled 36a, 36b, and 36c. Part 36a covers tab 20, part 36b covers body 12 and part 36c covers fingers 14 and 16. Layer 36 is composed of a paper backing with the side facing layer 34 covered with a coating, such as wax, to reduce the transfer of adhesive from layer 34 and allow for easy separation of the layers 34 and 36. Layer 36 is divided into a regions 36a, 36b and 36c by breaks 38 that extend through region 36. These breaks 38 permits separation of individual parts of layer 36 to expose the adhesive layer 34 below. Thus, the cannula guard 10, may be positioned on a patient's body without exposing the adhesive layer 34 located below the gauze layer 32 of the finger regions 14 and 16. Further, tab 20 may be either secured to the patient's skin or the layer 36a may be left in place to provide a tab for removing the cannula holder from the skin.

Figure 3:
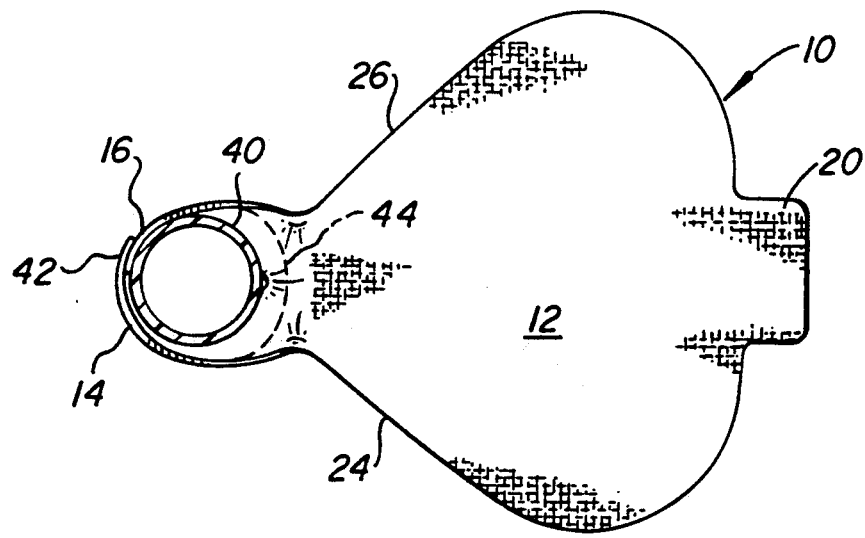
FIG. 3 is a top plan view of the holding device attached to a cannula.

Considering the overall operation of the cannula holder 10, FIG. 3 illustrates the holder 10 in use. A cannula 40 is inserted into an incision made by a trocar. Regions 36a and 36b of layer 36 are removed so that adhesive layer 34 is exposed. Medical personnel then position the holder 10 in proximity to the cannula 40 and secure the exposed portion of adhesive layer 34 to the patient's skin. Then region 36c is removed to expose the remainder of adhesive layer 34. Finger 16 is wrapped around one side of cannula 40 so that the adhesive layer 34 comes into binding contact with the outer surface of the cannula 40. Finger 14 is then wrapped around the other side of the cannula 40 so that adhesive layer 34 makes binding contact with the outer surface of the cannula. In a preferred embodiment, the fingers 14 and 16 are long enough to entirely engage the outer surface of the cannula 40 and to overlap as shown at 42. In an alternate embodiment, the fingers 14 and 16 do not overlap. When the fingers 14 and 16 surround the cannula 40, a fold line 44 is formed in layers 32 and 34. This fold line allows for the cannula to be easily adjusted with respect to the incision. The use of adhesive to attach the cannula holder to the skin does not traumatize the adjacent skin. This device has the additional advantages of being non-invasive and also providing for fast, easy application. Additionally, the cost associated with the device is significantly less than the prior art alternatives.

Although the present invention has been described by specific exemplary embodiments thereof, it will be understood by those skilled in the art that variations and modifications can be effected in these exemplary embodiments without departing from the scope and spirit of the invention.

What is claimed is:

1. A cannula holder for a cannula comprising a pad having a large surface area, a pair of fingers extending from one end of said pad and integrally formed with said pad, said fingers forming a V shaped configuration, first and second concave cut-out regions formed on the outer circumference of said pad on each side of the pad and disposed between the pad and the fingers to form an intermediate substantially reduced surface between the large surface area of the pad and the pair of fingers, a cannula, said fingers being wrapped around and secured to said cannula, the edge of the fingers being disposed at approximately a 90° angle with respect to the edge of the pad and the intermediate substantially reduced surface area having a fold line therein to permit angular adjustment of said cannula.

2. The device recited in claim 1 wherein said fingers are oriented so as to have an angle of approximately 80° between said first and second fingers.

3. The device recited in claim 1 wherein said first concave region has an angle of approximately 90° between said first finger and said pad.

4. The device recited in claim 1 wherein said second concave region has at an angle of approximately 90° between said second finger and said pad.

5. The device recited in claim 1 wherein said means for securing said cannula holder to a patient's skin comprises an adhesive layer integral with said pad.

6. The device recited in claim 5 wherein said means for securing said cannula to the cannula holder comprises an adhesive layer on said first and second fingers.

7. The device recited in claim 6 and further including means for securing said cannula to the cannula holder includes a paper layer.

8. The device recited in claim 7 wherein said paper layer has a wax layer substantially covering a surface facing of said pad.

9. The device recited in claim 8 wherein said paper layer is divided into a plurality of segments for allowing a user to expose select areas of said pad.

10. A cannula holder comprising:
   a pad having a large surface area and comprising a body portion and an intermediate portion;
   first and second finger shaped projections extending from said pad, said finger shape projections being integral with said pad and forming a V shaped region between said fingers and oriented so as to have an angle of approximately 80° between said first and second fingers;
   a first concave region formed on the outer circumference of said pad adjacent to said first finger for allowing said first finger to bend around an outer surface of a cannula where in the angle between said first finger and said pad is approximately 90°;
   an adhesive layer attached to a lower surface of said pad and fingers for securing said pad to a patient's skin and for securing said fingers to a cannula;
   said intermediate portion of the pad between said fingers and said body portion of said pad extending angularly between said body portion of said pad and said fingers, an intermediate portion of said layer remaining attached to said intermediate portion of said pad lacking said adhesive layer for allowing said intermediate portion to be unsecured with respect to the cannula and patient's skin so that the position of the cannula can be angularly adjusted; and
   a paper layer having a shape corresponding to said pad and fingers and having a wax coating substantially over a surface of said pad.

11. A method for securing a laparoscopic cannula disposed within an incision in a patient by means of a pad, the pad having a large surface area, a pair of fingers extending from one end of said pad and integrally formed with said pad, said fingers forming a V shaped configuration, concave cut-out regions formed on the outer circumference of said pad on each side of the pad and disposed between the pad and the fingers to form an intermediate substantially reduced surface area between the large surface area of the pad and the pair of fingers, the steps comprising adhering the pad to the skin of the patient adjacent the incision, lifting the fingers and bending the fingers around the laparoscopic cannula with the surface of the fingers being disposed at approximately 90° with respect to the surface of the pad, the intermediate substantially reduced surface area of the pad being unsecured with respect to the laparoscopic cannula and the patient's skin so as to form a fold line therein to permit the laparoscopic cannula to be adjusted angularly.

* * * * *